US011844966B2

(12) United States Patent
Goswami et al.

(10) Patent No.: US 11,844,966 B2
(45) Date of Patent: Dec. 19, 2023

(54) PLASMONIC PHOTOELECTROCHEMICAL OXIDATION FACE MASK

(71) Applicant: University of South Florida, Tampa, FL (US)

(72) Inventors: Dharendra Yogi Goswami, Tampa, FL (US); Dilip Neeraj Goswami, San Carlos, CA (US)

(73) Assignees: University of South Florida, Tampa, FL (US); MOLEKULE, INC., San Francisco, CA (US)

( * ) Notice: Subject to any disclaimer, the term of this patent is extended or adjusted under 35 U.S.C. 154(b) by 528 days.

(21) Appl. No.: 17/249,503

(22) Filed: Mar. 3, 2021

(65) Prior Publication Data
US 2021/0275838 A1    Sep. 9, 2021

Related U.S. Application Data

(60) Provisional application No. 62/984,643, filed on Mar. 3, 2020.

(51) Int. Cl.
| | |
|---|---|
| *A62B 7/10* | (2006.01) |
| *A61L 9/20* | (2006.01) |
| *A62B 7/12* | (2006.01) |
| *A62B 9/02* | (2006.01) |
| *A62B 18/00* | (2006.01) |

(Continued)

(52) U.S. Cl.
CPC .............. *A62B 7/10* (2013.01); *A61L 9/205* (2013.01); *A62B 7/12* (2013.01); *A62B 9/02* (2013.01); *A62B 18/006* (2013.01); *A62B 18/025* (2013.01); *A62B 18/10* (2013.01); *A62B 23/02* (2013.01); *B01J 35/004* (2013.01);

(Continued)

(58) Field of Classification Search
CPC ....... A62B 23/02; A62B 18/025; A62B 18/10; A62B 9/02; A62B 7/12; A62B 7/10; B01J 35/004; A61L 2209/111; A61L 2209/12; A61L 2209/14
See application file for complete search history.

(56) References Cited

U.S. PATENT DOCUMENTS

| | | |
|---|---|---|
| 2020/0030731 A1 | 1/2020 | Dhau et al. |
| 2020/0041418 A1 | 2/2020 | Wu et al. |

FOREIGN PATENT DOCUMENTS

| | | |
|---|---|---|
| JP | 2018047263 A | 3/2018 |
| WO | 2020032519 A1 | 2/2020 |

OTHER PUBLICATIONS

International Search Report and Written Opinion for PCT/US2021/070226 (International Filing Date: Mar. 3, 2021) dated Jun. 14, 2021; Applicant: University of South Florida.

(Continued)

*Primary Examiner* — Ophelia A Hawthorne
(74) *Attorney, Agent, or Firm* — Paul Murty; Smith & Hopen, P.A.

(57) ABSTRACT

A breathing system for removing harmful contaminants, such as microbes and volatile organic compounds, is provided. The breathing system includes a face mask, an inhalation limb, and a plasmonic device. As a contaminated gas flows through an internal chamber of the plasmonic device, the contaminates are oxidized. Specifically, the internal chamber includes a source of photons spaced apart from the nanostructure. The nanostructure is coated in a plasmonic layer, including noble metal nanoparticles. The plasmonic layer is protected from oxidation through a photocatalyst layer disposed thereon.

20 Claims, 12 Drawing Sheets

(51) Int. Cl.
    *A62B 18/02*     (2006.01)
    *A62B 18/10*     (2006.01)
    *A62B 23/02*     (2006.01)
    *B01J 35/00*     (2006.01)
    *B01J 35/02*     (2006.01)

(52) U.S. Cl.
    CPC ........ *B01J 35/023* (2013.01); *A61L 2209/111* (2013.01); *A61L 2209/12* (2013.01); *A61L 2209/14* (2013.01)

(56) References Cited

OTHER PUBLICATIONS

English Translation of Japanese Patent Application JP2018047263 with a publication date of Mar. 29, 2018.
English Translation of International Patent Publication WO 2020032519 A1 with a publication date of Feb. 13, 2020.
International Preliminary Report on Patentability dated Sep. 15, 2022 for PCT Application No. PCT/US2021/070226 with an International filing date of Mar. 3, 2021.

PLASMONIC PHOTOELECTROCHEMICAL OXIDATION FACE MASK

CROSS-REFERENCE TO RELATED APPLICATION

This nonprovisional application claims priority to U.S. Provisional Patent Application No. 62/984,643, entitled "Plasmonic Photoelectrochemical Oxidation Face Mask", filed on Mar. 3, 2020, the contents of which are herein incorporated by reference.

BACKGROUND OF THE INVENTION

1. Field of the Invention

This invention relates, generally, to devices for delivering clean air to a user. More specifically, it relates to a breathing system using a plasmonic photoelectrochemical oxidation air purification device for delivering clean, filtered gas to a user for personal protection from viruses, microbial agents, volatile organic compounds, and other environmentally harmful contaminants.

2. Brief Description of the Prior Art

In the age of COVID-19, disposable face masks are designed to be loosely disposed over a user's breathing passages. These disposable masks help prevent the spread of pathogens and diseases but have only limited effects on more dangerous contaminants, such as volatile organic compounds and smaller viruses. Moreover, disposable masks do not fit snugly around the wearers breathing passages and result in the user breathing in some amount of contaminated air with every breath.

For a higher level of protection against harmful contaminants, users can wear masks with filters, such as charcoal filters that seal around their face. However, while gas masks with filters are more effective at protecting users against some contaminants than disposable masks, they require routine filter changes to remain effective and do not protect against all contaminants. To achieve an even greater level of protection, users need to use expensive respirators with heavy and bulky compressed air or oxygen tanks to ensure complete safety. However, such systems are costly and require the tanks to be routinely filled. Moreover, the user can only use such systems as long as air remains in the tank.

Accordingly, what is needed is a portable breathing system that can remove harmful contaminants from contaminated air and deliver clean, filtered gas to the user for respiration without having to rely on dedicated air tanks or expensive disposable filters. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act, or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a portable plasmonic photoelectrochemical oxidation system for removing harmful contaminants from the air is now met by a new, useful, and nonobvious invention.

The novel structure includes a breathing purification system for delivering a filtered gas from an environment to a user. The breathing system includes an inspiration limb having a first end in fluid communication with a face mask. A second opposite end of the inspiration limb is similarly in fluid communication with a plasmonic device, such as a plasmonic photoelectrochemical oxidation device. A gas containing harmful contaminants is passed through an internal compartment of the plasmonic device. Once inside, the harmful contaminants are oxidized, thereby turning the harmful gas into a filtered gas. The internal compartment of the plasmonic device includes a source of photons having a wavelength. The source of photons may include a wavelength of 390 nm or less or a range of about 400-700 nm.

Spaced apart from the source of photons is a filter including a layer of nanostructures having a length that corresponds to about ⅓ to ¼ the wavelength emitted from the source of photons. In an embodiment, the nanostructure may be a carbon nanostructure, titanium dioxide nanostructure, or silicon dioxide nanostructure, or a transition metal or metal oxide nanostructure. Moreover, the nanostructure is coated with a layer of plasmonic nanoparticles. The plasmonic layer includes noble metal nanoparticles, such as silver nanoparticles or gold nanoparticles. Furthermore, to prevent the oxidation of the plasmonic layer and increase the efficiency of the overall system, a thin protective layer of a material is deposited onto the plasmonic layer via e-bream deposition, plasma deposition, or a chemical reaction. In an embodiment, the thickness of the protective layer is less than 5 nm. In yet another embodiment, the thickness of the protective layer is less than 1 nm.

In an embodiment, the nanostructure is crushed before applying the plasmonic nanoparticle layer. Crushing the nanostructure increases the available surface area for the plasmonic nanoparticle layer to be deposited, thereby increasing the breathing system's efficiency.

One embodiment of the present invention includes a method of removing harmful contaminants from a gas supplied to a user for respiration. A breathing system configured to supply an amount of filtered gas is provided. The breathing system includes an inspiration limb having a first end in fluid communication with a plasmonic device and a second end in fluid communication with a face mask. The plasmonic device includes an internal compartment having a source of photons spaced apart from a nanostructure. The nanostructure includes a plasmonic layer having noble metal nanoparticles. To prevent the oxidation of the noble metal nanoparticles and increase the efficiency of the system, a protective layer is disposed over the top of the plasmonic layer.

Moreover, the gas containing harmful contaminants is passed through the internal compartment where the harmful components are oxidized before flowing into the inspiration lumen. A one-way valve is provided having a closed configuration and an open configuration. The closed configuration occurring when there is a positive pressure within the inhalation limb, and the open configuration occurring when there is a negative pressure within the inspiration limb. In the open configuration, the filtered gas flows from the internal compartment through the inhalation limb and into the face mask of the user.

These and other important objects, advantages, and features of the invention will become clear as this disclosure proceeds.

The invention accordingly comprises the features of construction, combination of elements, and arrangement of parts that will be exemplified in the disclosure set forth hereinafter, and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a breathing purification system for ensuring the air a user (or patient) breathes is clean and free of harmful contaminants. Contaminants can range from toxic chemicals to microbes, such as viruses, bacteria, and spores that can result in the disease, sickness, or even death of the user. The plasmonic photoelectrochemical oxidation (plasmonic PECO) device utilizes photons (i.e., light) to enable a semiconductor to promote catalytic oxidation to filter a gas (such as atmospheric air). This filtered gas is then supplied to the user for respiration. In particular, a gas containing harmful contaminants passes through the plasmonic PECO device's internal compartment via the operation of a fan, which is controlled by a switch. As the contaminated gas passes through the internal compartment to the inspiration limb, the harmful contaminants are removed via oxidation—turning the harmful gas into a filtered gas. The filtered gas is then permitted to flow through the inspiration limb and to the face mask, where it becomes available to be used by the user for respiration.

Breathing System

Figure 1:
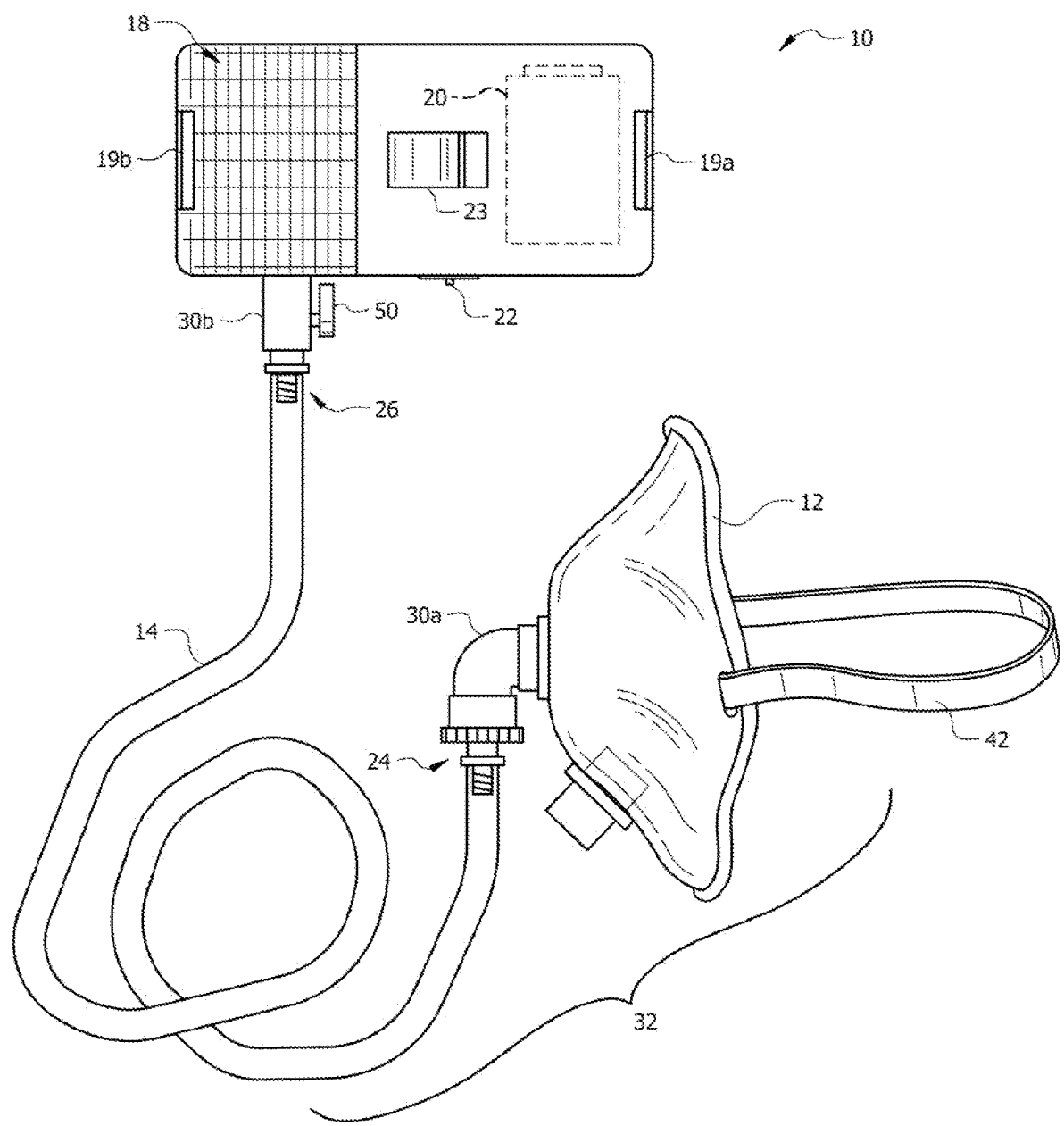
FIG. 1 is a top view of the breathing system for removing harmful contaminants from a gas.

FIG. 1 is a top view of breathing system 10. System 10 includes face mask 12, inspiration limb 14, and plasmonic PECO device 16 (including fan 18, power source 20, switch 22, and attachment mechanism 23). Face mask 12 is mechanically coupled to first end 24 of inspiration limb 14 so that a gas (such as air, oxygen, nitrogen, or a combination of breathable gases) is permitted to flow between face mask 12 and inspiration limb 14. Although elbow fitting 30a is shown in FIG. 1, in other embodiments, one or more additional coupling mechanisms may be provided to couple first end 24 of inspiration limb 14 to face mask 12. Such additional coupling mechanisms may include straight fittings, quick disconnect fittings, magnetic coupling, or any other mechanism known in the art.

Second end 26 of inspiration limb 14 is similarly coupled to plasmonic PECO device 16 via fitting 30b. In an embodiment, one or more additional coupling mechanisms may be provided to couple second end 26 of inspiration limb 14 to plasmonic PECO device 16. Such additional coupling mechanisms may include straight fittings, quick disconnect fittings, magnetic coupling, or any other mechanism known in the art. In such configurations, a filtered gas flows from plasmonic PECO device 16, through inspiration limb 14, and to face mask 12, where the filtered gas is used for respiration by the user. Moreover, the flow of the filtered gas may be facilitated by operation of fan 18 in electrical communication with power source 20 (such as a battery). The operation of fan 18 helps facilitates the flow of the gas through plasmonic PECO device 16 and to face mask 12 worn by the user. Moreover, system 10 may include switch 22 to control the flow of electricity to fan 18 and additional electrically powered components, which will be discussed in greater detail below.

Non-porous flexible polymers or non-porous metal foil may be used to construct face mask 12 and inspiration limb 14 (collectively flow components 32). In an embodiment, flow components 32 may be transparent or opaque and constructed from one or more materials, such as acrylonitrile-butadiene-styrene (ABS), latex, polyvinylchloride (PVC) thermoplastics, non-woven fabric, polypropylene, or other suitable known in the art. In yet another embodiment, such as those where flow components 32 are constructed using non-woven fabrics, a chemical compound or substance toxic to microorganisms (e.g., antimicrobial agents, synthetic chemicals, antibiotics, poisons, or metabolic products) may be woven into, impregnated, or coated with at least a portion of flow components 32 to help reduce or prevent the growth and spread of microorganisms on flow components 32, thereby further reducing the risk of infection to the user.

Face Mask

Figure 2A:
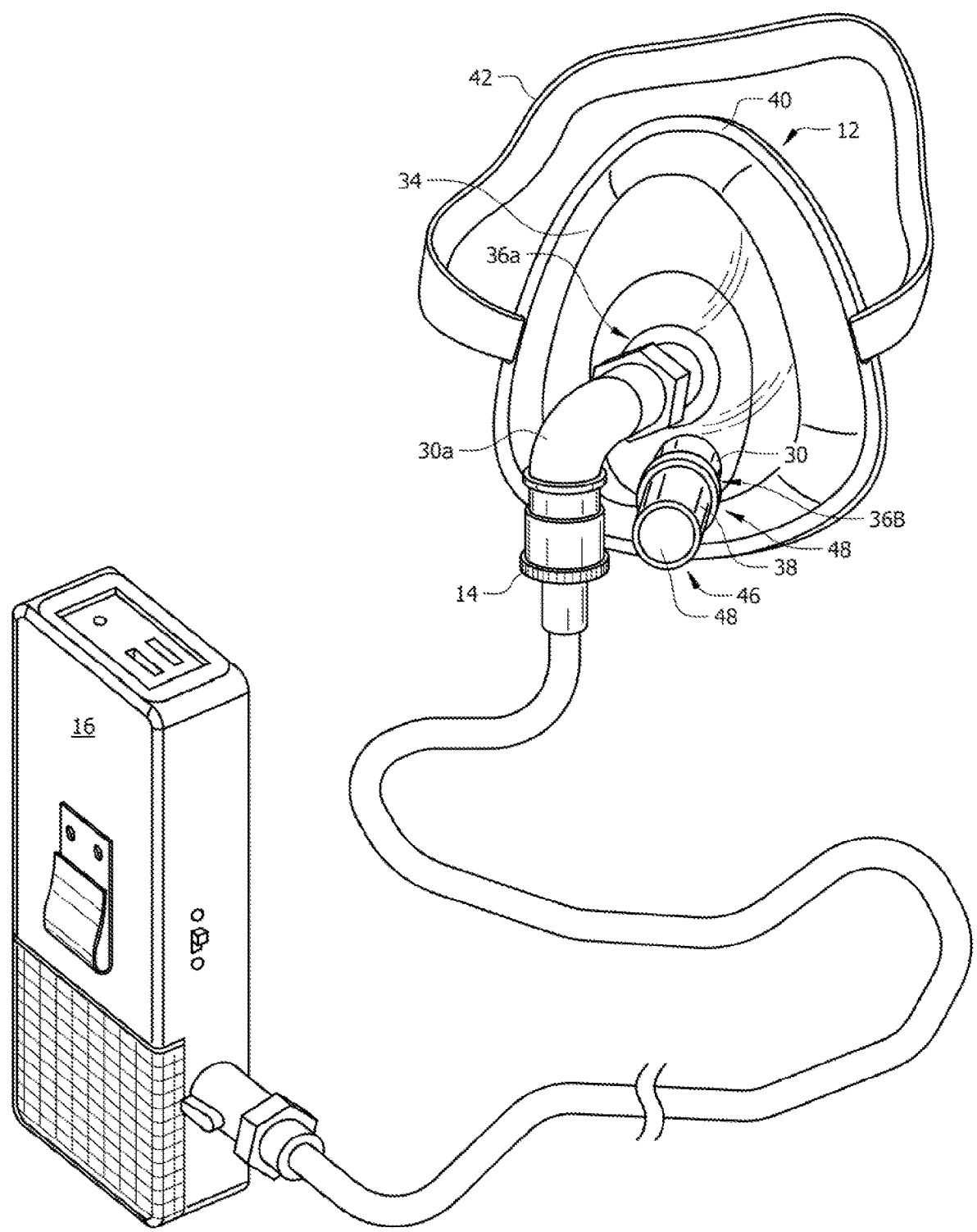
FIG. 2A is a perspective view of an embodiment of a face mask.

FIG. 2A depicts an embodiment of face mask 12, which features body 34, inhalation port 36a, exhalation port 36b (collectively ports 36), fitting 30a, inhalation limb 14, exhalation limb 38, gasket 40, and strap 42. Face mask 12 is configured to be worn over the user's breathing passages, such that the user's nasal and oral passages are covered and isolated from the external environment. Face mask 12 may contour to the user's face so that harmful contaminants (e.g., environmental pollutants, viruses, microbial agents, volatile organic compounds (VOCs), and other harmful substances) are prevented from unintentionally entering or exiting face mask 12.

Ports 36A and 36B are disposed through body 34 of face mask 12 and mechanically engage with inhalation limb 14 and exhalation limb 38 respectively via fitting 30a and 30b (see FIG. 1). In use, filtered gas is supplied by plasmonic PECO 16 to the user via inhalation limb 14 for inspiration. Moreover, inhalation port 36a may be disposed proximal to the user's nasal passages and may include an optional nasal gasket to seal the inhalation port 36a to the user's nose creating a dedicated inhalation circuit. Furthermore, exhalation port 36b may be disposed proximal to the user's oral passageway. The positioning of inhalation port 36a and exhalation port 36b in proximity with their respective passageways, helps facilitate the user's respiration. Specifically, during respiration, the user would inhale through their nose and exhale through their mouth. Placement of ports 36 near their respective anatomical structures helps reduce the amount of rebreathing that may occur.

Once the user's inspiration phase of the breathing cycle is complete, the expired gas from the user resulting from the user's exhalation phase is exhausted away from the user via exhalation limb 38. Exhalation limb 38 extends outwardly away from body 34 from first end 44 to second end 46. Positioned at second end 46 of exhalation limb 38 is exhaust valve 48. Exhaust valve 48 is configured to control the flow of the exhalation gas formed as a by-product of the user's natural respiration. In an embodiment, exhaust valve 48 may be a flap that covers the opening of the exhalation limb and prevents particles, microbes, VOCs, or other harmful contaminants from passing through exhaust valve 48 and into exhalation limb 38 when closed. Specifically, exhaust valve 48 prevents the backflow of gas from the external environment when face mask 12 is properly secured to the user by strap 42.

Strap 42, such as an elastomeric strap, is used to secure face mask 12 to the user. Strap 42 can be placed over the ears of and around the user's head. To further fasten face mask 12 to the user's head, strap 42 may be pulled tight so that atmospheric (i.e., external or contaminated) air cannot pass between face mask 12 and an internal environment formed when face mask 12 is securely fastened to the user's head. In an embodiment, face mask 12 may be secured using one or more straps 42, clips, dermal adhesive, or by other materials and methods known in the art.

To ensure an airtight seal between face mask 12 and the user, gasket 40 may be provided. Gasket 40 helps prevent the user from being exposed to contaminated air from the environment because of an improper seal or air leak. Gasket 40 is disposed about the perimeter of face mask 12 and may be made of paper, rubber, silicone, metal, cork, felt, neoprene, nitrile rubber, rubber, fiberglass, polytetrafluoroethylene, or other suitable material for creating an airtight seal between face mask 12 and the user.

Figure 2B:
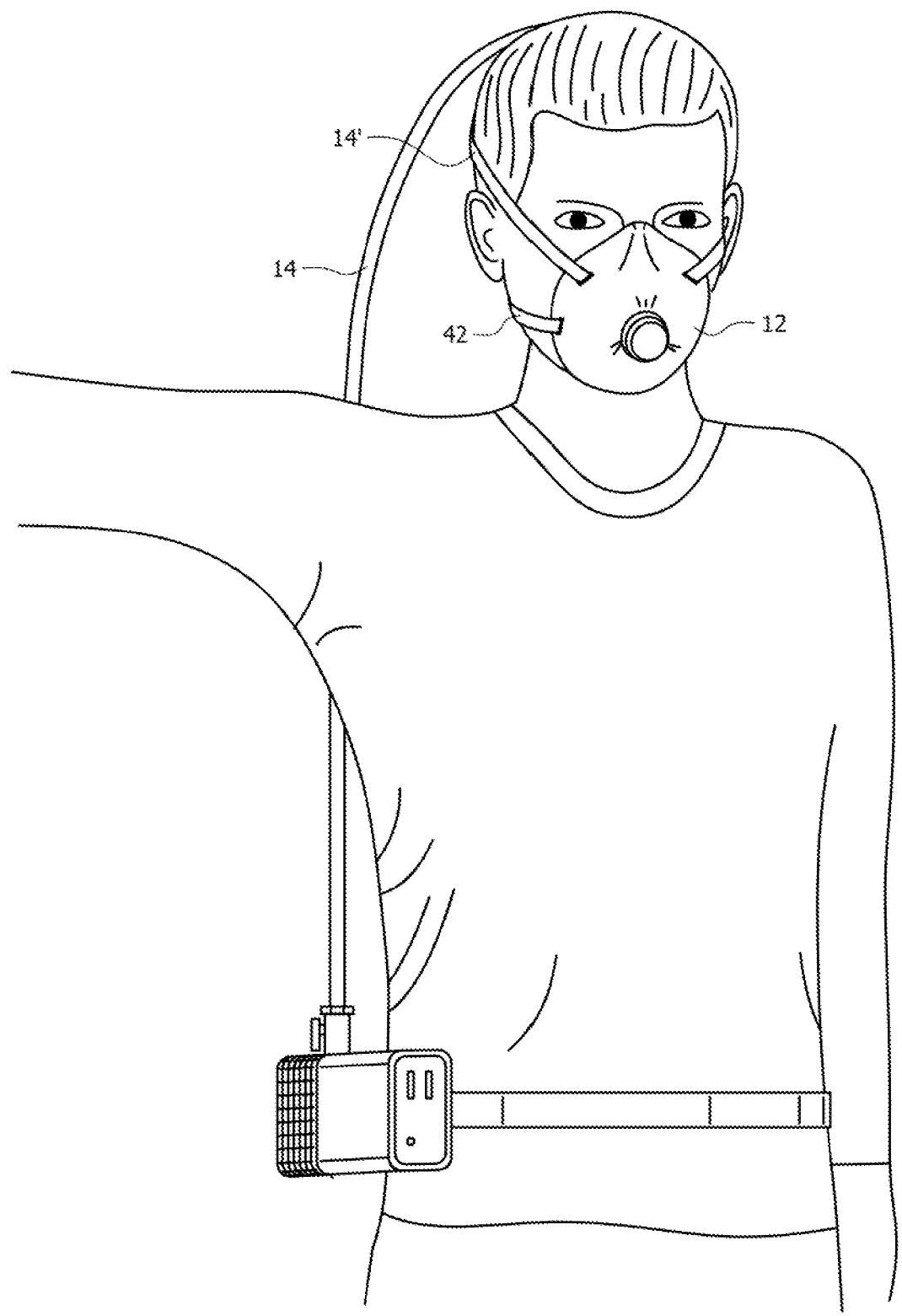
FIG. 2B is an in-use embodiment of the breathing system securely fastened to a user.

FIG. 2B depicts an embodiment of face mask 12 securely fastened to the user's head via strap 42. To provide users with increased mobility and reduce the equipment positioned in front of the user's face, inhalation limb 14 is securely fastened at the back of the user's head. To deliver the filtered gas flowing within inhalation limb 14 to face mask 12, secondary inhalation limb 14' is provided. Specifically, secondary inhalation limb 14' delivers filtered gas from inhalation limb 14 to face mask 12 of the user. While secondary inhalation limb 14' may provide some degree of fastening of face mask 12 to the user, strap 42 is provided to ensure that face mask 12 is securely fastened to the user.

Inhalation Limb

Figure 3A:
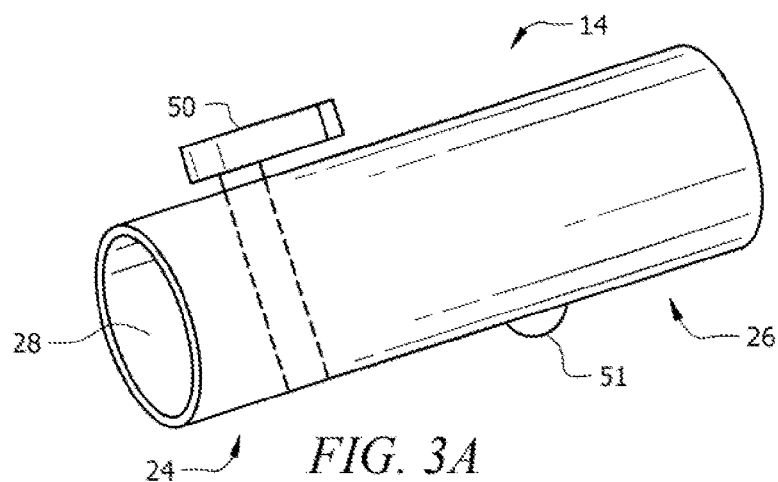
FIG. 3A is a perspective view of an embodiment of an inspiration limb.
Figure 3B:
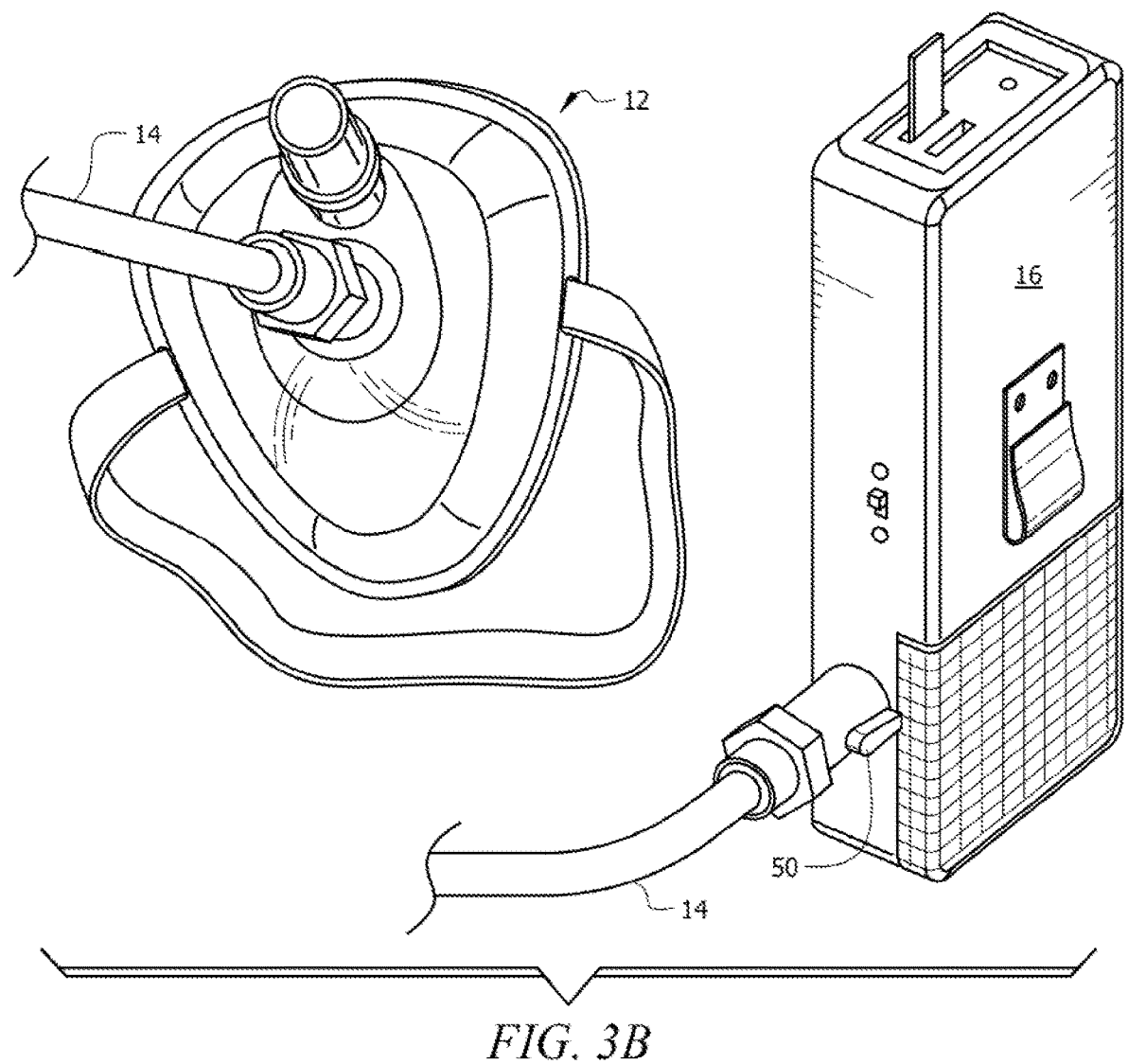
FIG. 3B is a perspective view of an embodiment of the breathing system.
Figure 4A:
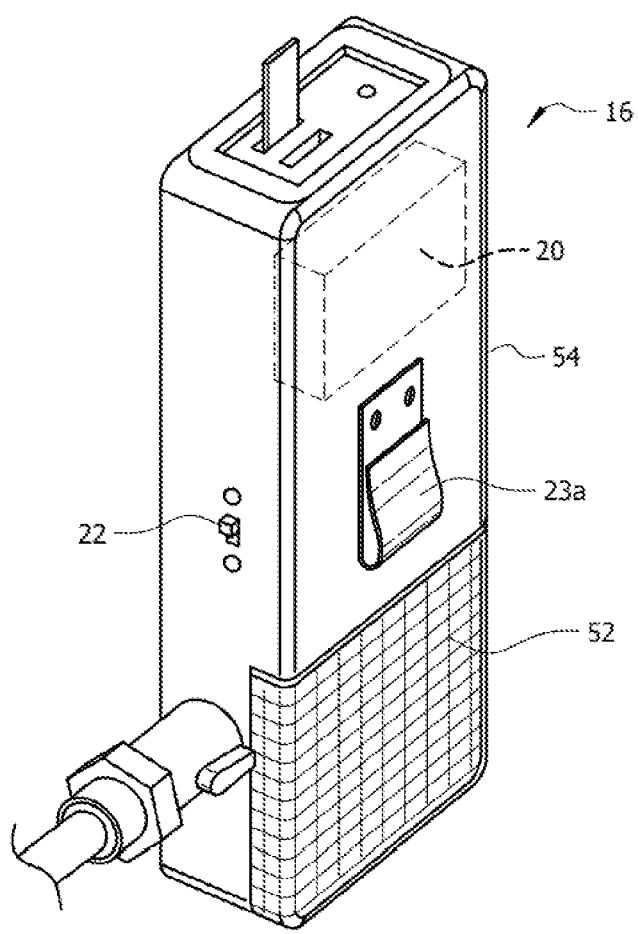
FIG. 4A is a perspective view of an embodiment of a plasmonic photoelectrochemical oxidation device.
Figure 4B:
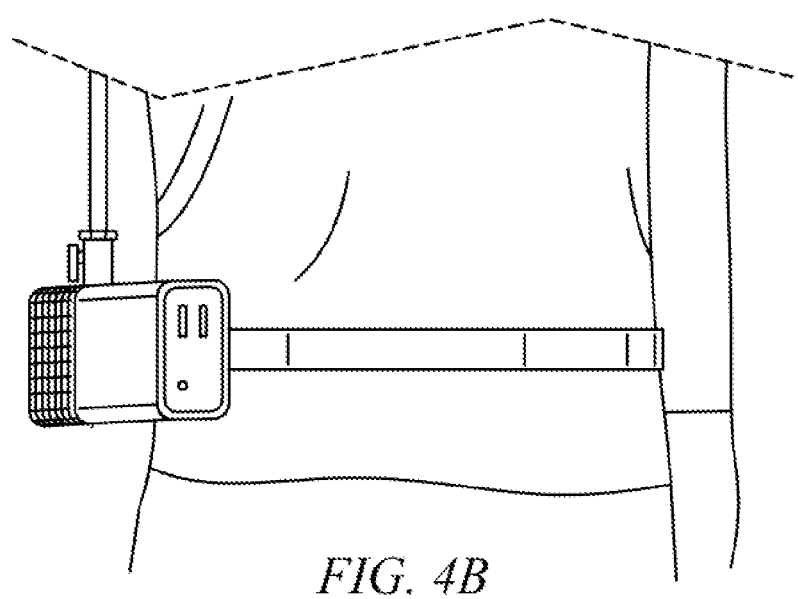
FIG. 4B is a perspective view of an embodiment of the plasmonic photoelectrochemical oxidization device securely fastened to a user by a belt.
Figure 4C:
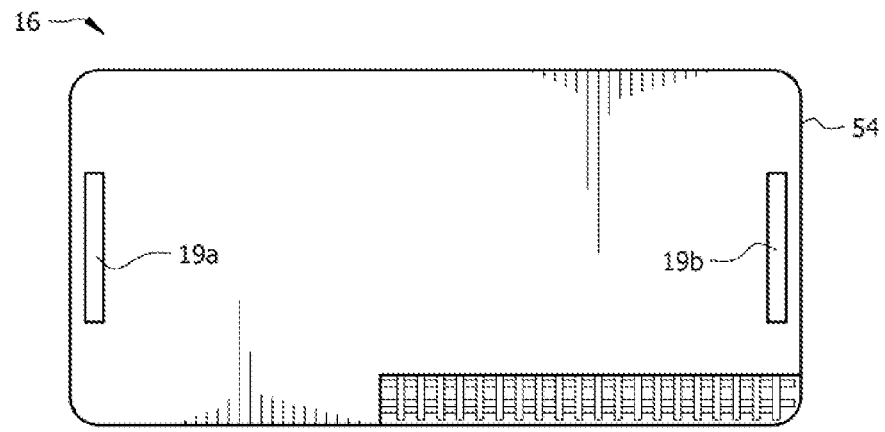
FIG. 4C is a side view of the plasmonic photoelectrochemical oxidization device of FIG. 4B.
Figure 4D:
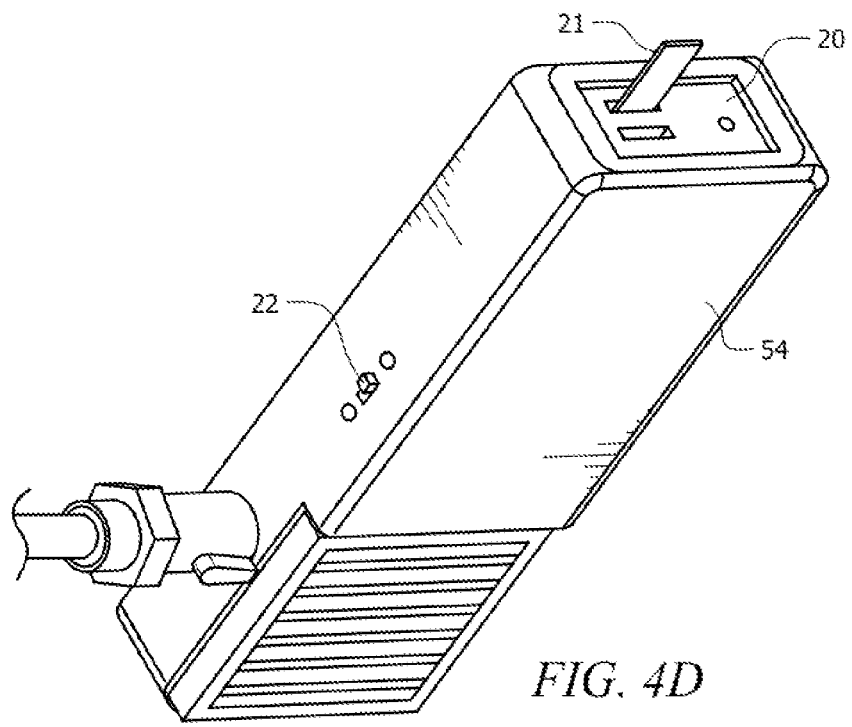
FIG. 4D is a perspective view of an embodiment of the plasmonic photoelectrochemical oxidization device.

FIGS. 3A and 3B depict inhalation limb 14. Inhalation limb 14 includes lumen 28 extending between first end 24 and second end 26. Inhalation limb 14 may include inhalation valve 50 disposed between first end 24 and second end 26 of inhalation limb 14. Inhalation valve 50 is configured to regulate the flow of the filtered gas through inspiration lumen 28. In an embodiment, inhalation valve 50 is a one-way valve such as a solenoid valve, a regulation valve, a butterfly valve, a check valve, a gate valve, or a similar type of valve that permits the regulation of filtered air.

In an embodiment, inhalation valve 50 may be a flap valve that requires minimal pressure to open in the opening direction. For example, when a user inhales, the negative pressure created within inhalation limb 14 permits inhalation valve 50 to open, thereby supplying filtered air to the user. When the user exhales, the pressure inside inhalation limb 14 changes to positive pressure. This positive pressure forces inhalation valve 50 to shut. When the user draws a breath, inhalation valve 50 is opened via the negative pressure generated on the opposite side of inhalation valve 50, thereby permitting the filtered gas to flow to the user for respiration. When a user subsequently exhales, the positive pressure generated by the user's exhalation breath forces inhalation valve 50 to close. The closure of inhalation valve 50 prevents the backflow of the user's exhalation gas (i.e., exhaled breath).

Furthermore, inhalation limb 14 may be formed of an expandable material to prevent the rupture of inhalation limb 14 because of over-pressurization. In embodiments when inhalation valve 50 is closed, fan 18 of plasmonic PECO device 16 (see FIG. 4) still forces filtered gas into inhalation limb 14. As the filtered gas is continually forced into inhalation limb 14, inhalation limb 14 is forced to expand to prevent rupture and maintain a predetermined pressure as measured by pressure sensor 51. When pressure sensor 51 detects a pressure reading above the predetermined level, it signals switch 22 to shut down fan 18 of plasmonic PECO device 16. Once the pressure returns to a normal operating pressure as determined by the user or the user inhales, pressure sensor 51 signals switch 22 to resume the normal operation of plasmonic PECO device 16, including fan 18.

Plasmonic PECO Device

FIGS. 4A-4F depict plasmonic PECO device 16. Plasmonic PECO device 16 includes grate 52, power source 20, switch 22, and attachment mechanism 23.

Attachment Mechanism

Attachment mechanism 23 is configured to removably secure plasmonic PECO device 16 to the user for increased portability and ease of use. Attachment mechanism 32 may include clip 32a, configured to removably couple plasmonic PECO device 16 to belt 17. In an embodiment, belt 17 may be disposed at least partially through one or more apertures 19a and 19b, thereby securing plasmonic PECO device 16 to belt 17 worn by the user.

In embodiments in which plasmonic PECO device 16 is configured to be a portable system, power source 20 can be configured as a battery, such as a 12V or 24V battery, to provide power to plasmonic PECO device 16. Power source 20 may be disposed external to housing 54 or may reside within housing 54, such that power source 20 is protected from damage. In such embodiments in which power source 20 is disposed within housing 54, power source 20 may include graspable portion 21 extending outward from housing 54. Graspable portion 21 allows for the easy removal of power source 20 from within housing 56. In an embodiment, power source 20 may be a photovoltaic cell, power cord, or any other mechanism or device known in the art to supply an amount of power to plasmonic PECO device 16.

Grate

Figure 5A:
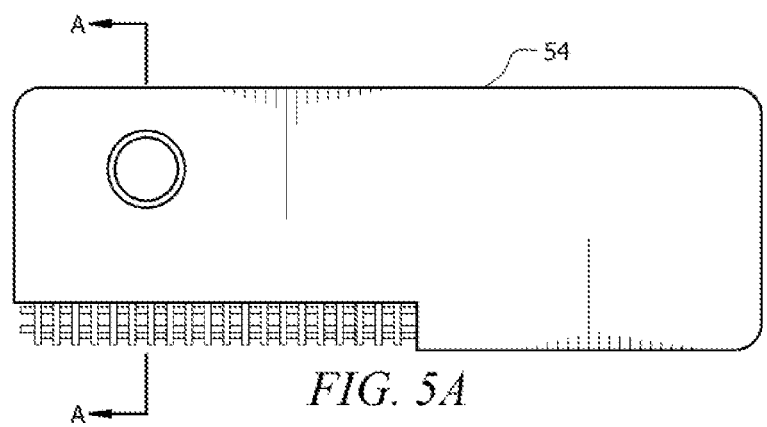
FIG. 5A is a top view of an embodiment of the plasmonic photoelectrochemical oxidization device.
Figure 5B:
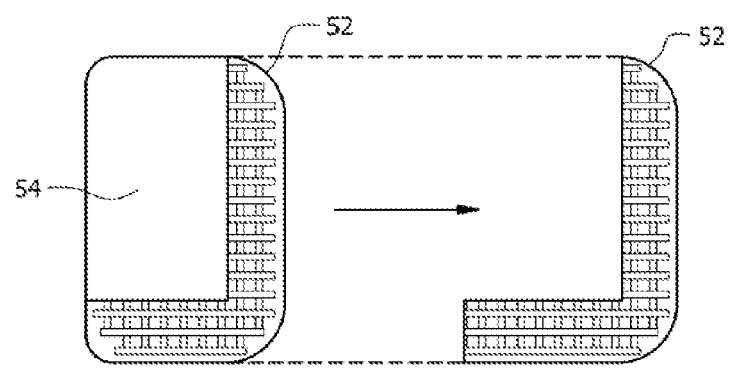
FIG. 5B is a side view of the plasmonic photoelectrochemical oxidization device of FIG. 5A.

As shown in FIGS. 5A and 5B, grate 52 is disposed on, adjacent to, or coupled with housing 54. Grate 52 prevents damage to internal components, such as pre-filter 53, filter 59, and/or fan 18, as a result of large objects being drawn into the internal compartment by fan 18. Internal components will be discussed in greater detail in FIGS. 5A and 5B. Grate 52 may also help prevent injury to the user if the user's fingers are accidentally inserted within internal compartment 56 during operation. Grate 52 may be removable, such that grate 52 can be removed from housing 54 to expose pre-filter 53 and/or filter 59. Having a removable grate 52 allows the user to easily access internal compartment 56 and swap and/or clean pre-filter 53 and/or filter 59.

Figure 6A:
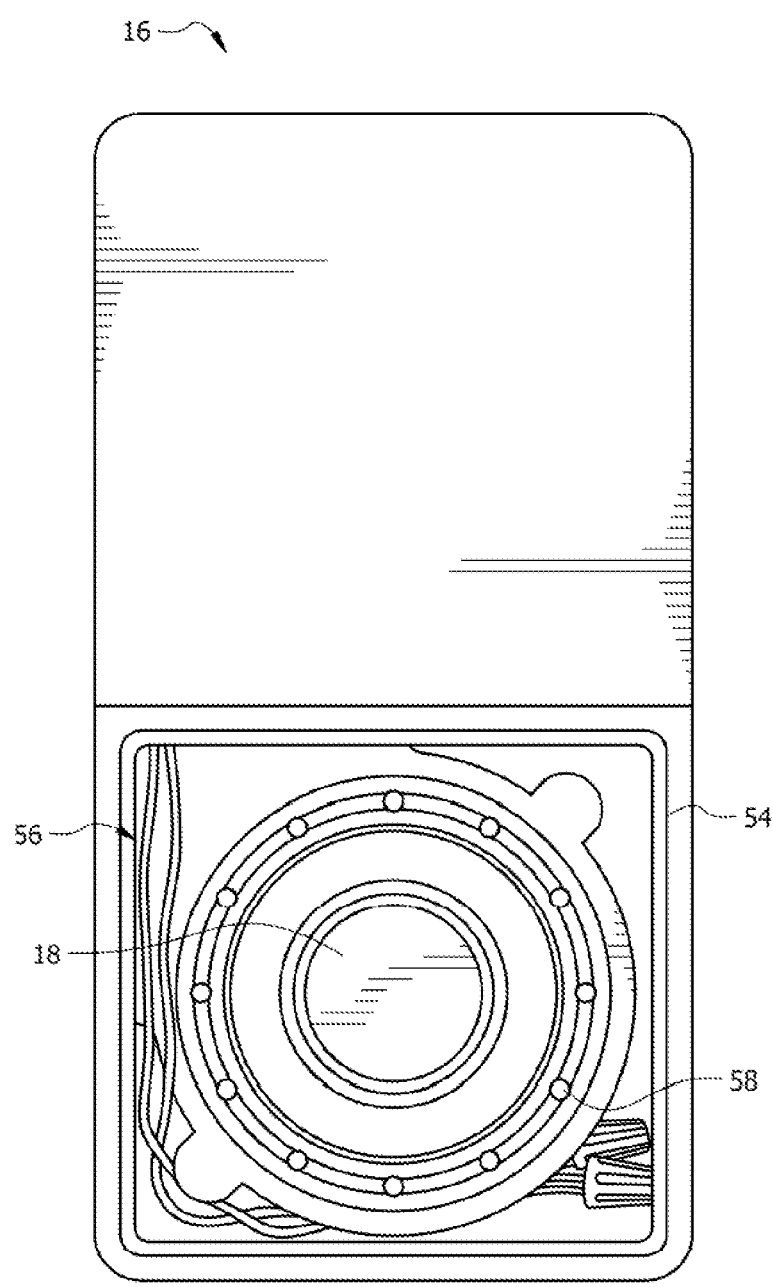
FIG. 6A is a top view of an embodiment of a plasmonic photoelectrochemical oxidization device with the grate, prefilter, and filter removed from view.
Figure 6B:
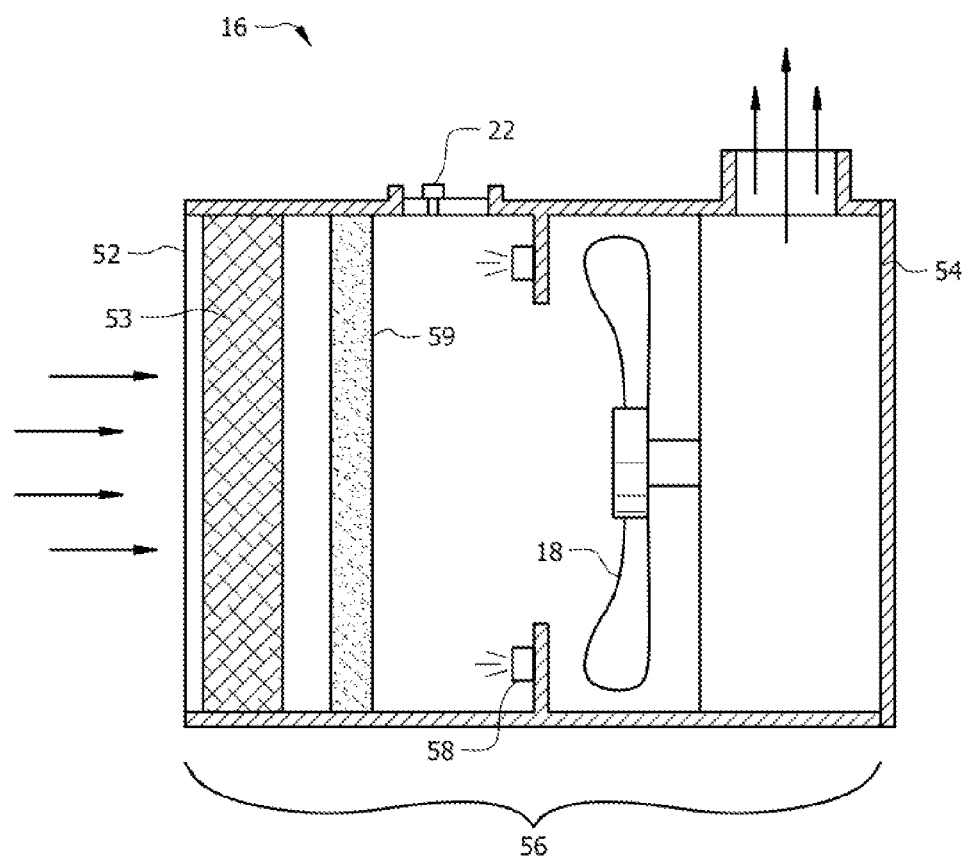
FIG. 6B is a side cut away view of the plasmonic photoelectrochemical oxidization device taken along line A-A of FIG. 5A showing the internal compartment.

Details of an embodiment of internal compartment 56 are shown in FIGS. 6A-6B. Specifically, FIGS. 6A and 6B depict internal compartment 56 of plasmonic PECO device 16. Positioned within internal compartment 56 is pre-filter 53, plasmonic PECO filter 59, light source 58, and fan 18. During the operation of plasmonic PECO device 16, fan 18 draws contaminated air in from the environment and into internal compartment 56. Specifically, as contaminated air is drawn through grate 52, pre-filter 53, and plasmonic PECO filter 59, the harmful contaminants are removed from the contaminated air, thereby creating clean, filtered air for the user to breathe. The operation of fan 18 is controlled by switch 22, which controls the flow of electricity from power source 20 to fan 18 and components residing within internal compartment 56.

Pre-Filter

As contaminated air passes through grate 56, the contaminated air is drawn through pre-filter 53 to filter out dust particles and other large objects that may have made it through grate 52. Pre-filter 53 is constructed of materials that absorb volatile organic compounds, viruses, microbial agents, and other environmentally harmful contaminants. Pre-filter 53 may be coated with a photocatalyst and plasmonic particles that are configured to be reactive to light—including visible light. In an embodiment, pre-filter 53 is a high-efficiency particulate air (HEPA) filter, carbon filter, chemical filter, antimicrobial filter, or other filters known in the art to filter and purify the air from harmful contaminants.

Plasmonic PECO Filter

Once the air is drawn through pre-filter 53, it is subsequently drawn through plasmonic PECO filter 59 to remove any remaining contaminants from the contaminated air, thereby ensuring safe, clean, and filtered gas is delivered to the user. Plasmonic PECO filter 59 includes a substrate coated with plasmonic nanostructures that are reactive to photons emitted from light source 58. Specifically, the photons initiate a reaction on the coated substrate to clean the air of harmful contaminants. During operation, most of the photons emitted by the light source are absorbed within the photocatalyst layer. However, some photons may be absorbed within the plasmonic layer. The photons react with the photocatalyst to release electrons thereby forming a positive hole from where they came. The plasmons from the plasmonic layer prevent the electrons from returning to the positive hole long enough for the oxidization reaction to occur which removes the harmful contaminates from the gas. Once the oxidization reaction is complete, the electrons are returned to their gaps, thereby reforming a stable neutral charge.

In an embodiment, pre-filter 53 and plasmonic PECO filter 59 are spaced apart from one another. In an embodiment, pre-filter 53 and plasmonic PECO filter 59 are disposed adjacent to one another.

Light Source

Light source 58 is spaced apart from plasmonic PECO filter 59, such that the photons emitted by light source 58 are incident on plasmonic PECO filter 59. Light source 58 emits light (i.e., photons) in a wavelength range that is dependent on the particular light source 58 used. For example, blacklight bulbs emit in a range of about 320 nm to 400 nm with a peak at 365 nm. Alternatively, light emitting diode (LED) sources of light emit a narrower wavelength range of about 360 nm to 400 nm. Furthermore, embodiments utilizing visible light (about 400 nm to 700 nm) and ultraviolet-A (UV-A) are also provided.

Construction of Plasmonic PECO Filter

Figure 7A:
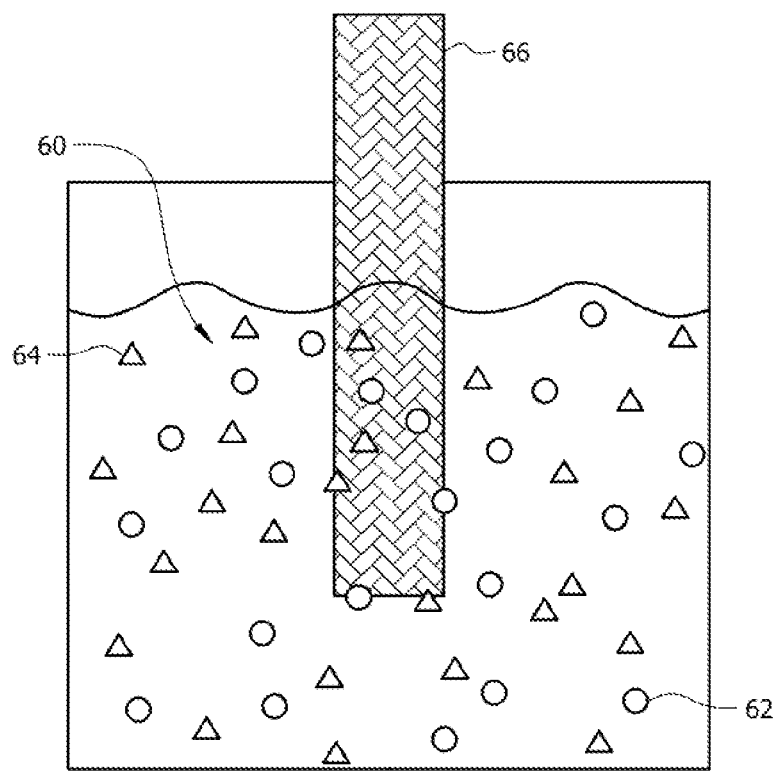
FIG. 7A is an illustration of the substrate being inserted within a slurry containing a photocatalyst and plasmonic nanoparticles.
Figure 7B:
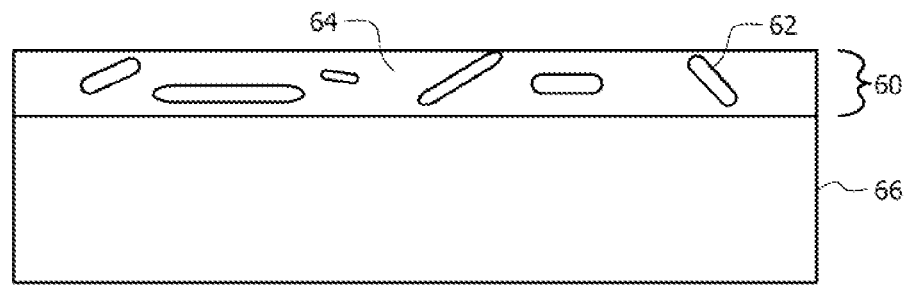
FIG. 7B is a diagram of the plasmonic PECO filter illustrating the layering of the dried slurry on the substrate.

As shown in FIGS. 7A and 7B, plasmonic PECO filter 59 is formed by coating, impregnating, or otherwise disposing slurry 60 (e.g., mixture) comprising plasmonic nanostructures 62 and photocatalyst 64 onto substrate 66. Slurry 60 contains plasmonic nanostructures 62, photocatalyst 64, and a volatile liquid (e.g., deionized water). In an embodiment, slurry 60 also includes a surfactant (e.g., isopropyl alcohol) to keep plasmonic nanostructures 62 and photocatalyst 64 separate from one another, thereby increasing the available surface area. Without the surfactant, plasmonic nanostructures 62 may stick to one another resulting in less surface area and prevent photocatalyst 64 from surrounding the plasmonic nanostructures 62 completely. Plasmonic nanostructures 62 are mixed with photocatalyst 64 in a ratio (plasmonic nanostructures:photocatalyst) of 1:1000 or 1:10. In an embodiment, plasmonic nanostructures 62 are mixed with photocatalyst 64 in a ratio of 1:100. In an embodiment, the ratio of plasmonic nanostructures 62 to photocatalyst 64 can range from 1:1000 to 1:10. Once slurry 60 is created using the desired ratio of plasmonic nanostructures 62 to photocatalyst 64, substrate 66 is then coated with slurry 60 and dried. During the drying process, the volatile liquid evaporates, leaving the plasmonic nanostructures 62 and photocatalyst 64 dried on substrate 66, forming plasmonic PECO filter 59.

Substrate 66 can be fibers of a fibrous material, a metal sheet, spun fiberglass material, pleated paper, washable fabric, pleated fabric, and plastic. Plasmonic PECO filter 59 is constructed by coating, impregnating, or otherwise disposing slurry 60 on substrate 66. In an embodiment, substrate 66 may be coated with a layer of plasmonic nanoparticles 62 and subsequently coated with a layer of photocatalyst 64 to prevent the development of a thick photocatalyst 64 layer that can result when using slurry 60.

Figure 8:
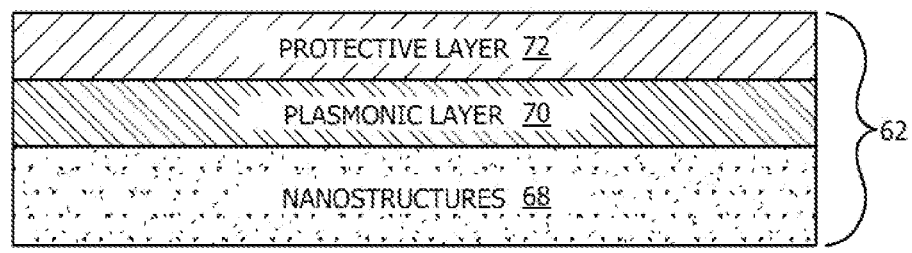
FIG. 8 is a diagram depicting an embodiment of the layering of the plasmonic layer and the protective layer on a nanostructure.

As depicted in FIG. 8, nanostructures 68, including nanorods and nanotubes, are preferably constructed from titanium oxide, silicon oxide, or other materials known in the art to create nanostructures 68. Nanostructures 68 are arranged in a random configuration or may be arranged in specific configurations, such as chiral, armchair, or zig-zag. The size (e.g., length) of nanostructures 68 corresponds to about $\frac{1}{3}$ to $\frac{1}{4}$ the wavelength of light emitted from light source 58 (see FIG. 5B). For example, plasmonic PECO device 16 utilizing a LED light source emitting a wavelength of 360 nm to 400 nm may have a length of about 90 nm to 132 nm. In an embodiment, the size of nanostructures 68 is 50 nm to 100 nm. Alternatively, plasmonic PECO device 16 utilizing visible light with a wavelength of 400 nm to 700 nm may include nanostructures 68 with a length of about 100 nm to 231 nm.

Furthermore, plasmonic layer 70 comprising noble metal nanoparticles, such as silver nanoparticles, is applied to nanostructures 68 by e-beam deposition or plasma deposition. Plasmonic layer 70 is coated with protective layer 72 to prevent plasmonic layer 70 from being oxidized. For example, silver is readily oxidized in the presence of oxygen. To prevent the oxidization of silver (or other metals) from occurring and thereby retain the system's effectiveness, plasmonic layer 70 is fully coated with protective layer 72. Protective layer 72 may be an oxide (e.g., silicon oxide), a hydride (e.g., boron hydride), a salt (e.g., sodium nitrate), or a photocatalyst layer. In an embodiment, the thickness of protective layer 72 is less than 50 nm. In an embodiment, the thickness of protective layer 72 is less than 5 nm. In an embodiment, the thickness of protective layer 72 is less than 1 nm to reduce surface layer oxidation. In an embodiment, plasmonic layer 70 may include only the metal nanostructures coated with protective layer 72.

In an embodiment in which a photocatalyst is used as part of protective layer 72, the photocatalyst must completely cover plasmonic layer 70 and be non-porous to protect plasmonic layer 70 from oxidization.

Alternatively, in an embodiment, plasmonic layer 70 is deposited on nanostructures 68 via a reduction reaction of a salt of the metal nanoparticles used. For example, when plasmonic layer 70 includes silver nanoparticles, plasmonic layer 70 is applied to nanostructures 68 via a silver halide reduction reaction. In such embodiments, in which plasmonic layer 70 is applied via a reduction reaction, the photocatalyst layer is not necessary (although optional) to protect plasmonic layer 70 from surface layer oxidation as a product of the reduction reaction may cover plasmonic layer 70.

Furthermore, the photocatalyst's performance can be improved by doping the photocatalyst with nitrogen or metal nanoparticles. In an embodiment, the photocatalyst is a semiconductor, such as titanium dioxide or silicon dioxide. In an embodiment, the photocatalyst can be titanium oxide or zinc oxide. In yet another embodiment, the photocatalyst is titanium oxide doped with nitrogen or metal nanoparticles for activation by visible light photons.

Figure 9:
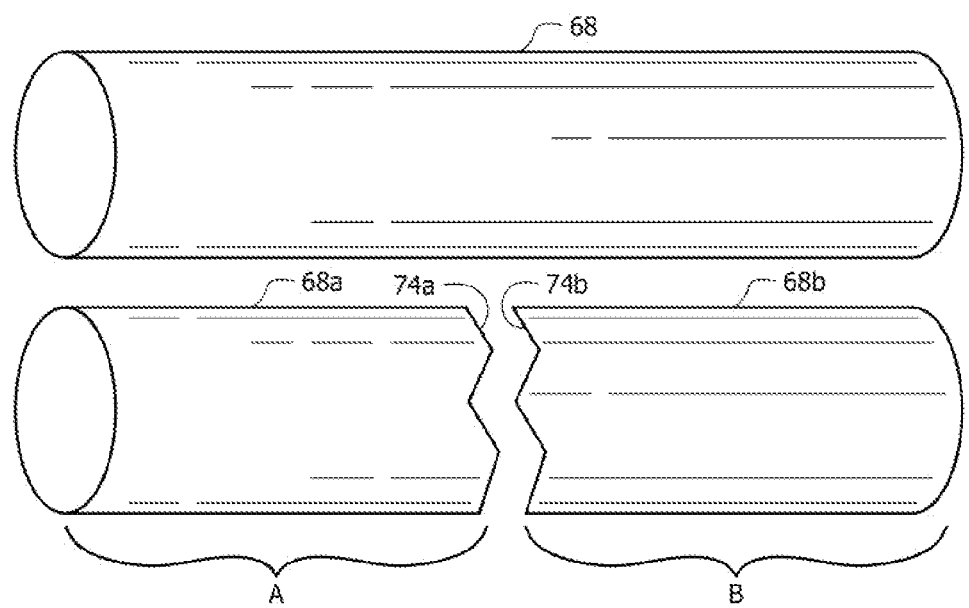
FIG. 9 is a diagram illustrating the crushing of a nanostructure.

As shown in FIG. 9, nanostructures 62 may be crushed prior to being coated with the photocatalyst. Crushed nanostructures 62 increase the available surface area for the photocatalyst to be applied, thereby increasing the efficiency of breathing system 10. In particular, when nanostructures 68 are crushed, nanostructures 68 are separated (or cracked) into smaller segments 68a and 68b, such that nanostructures 68 retain their original shape (e.g., rod or cylindrical shape) as shown in FIG. 9. For example, when a nanorod is crushed, it is broken into smaller segments A and B while retaining its original cylindrical shape. At the points of crushing, two new surfaces, 74a and 74b, are exposed having a randomly shaped surface area, which increases the total surface area available for the photocatalyst to be deposited on. In an embodiment, crushed nanostructures 68 have a length in the range of 50 nm to 100 nm and a corresponding nanoparticle size of 10-20 nm or more as measured length wise via electron microscopy.

In yet another embodiment, plasmonic layer 70 may be mixed with the photocatalyst. The mixing of plasmonic layer 70 with the photocatalyst layer results in some of the plasmonic particles being in the same layer as the photocatalyst or even below the photocatalyst layer.

Accordingly, as a gas containing harmful contaminates flows into internal compartment 56 of plasmonic PECO device 16, the catalytic oxidation of the harmful contaminants occurs. The speed at which the photoreaction occurs (e.g., photocatalysis) can be increased by using the photocatalyst. The photons emitted by light source 58 enable a semiconductor to promote the catalytic oxidation that purifies the gas containing the harmful contaminates into a safe, filtered gas. The filtered gas then flows through the inhalation limb 14 and to face mask 12 for use during respiration.

Figure 10:
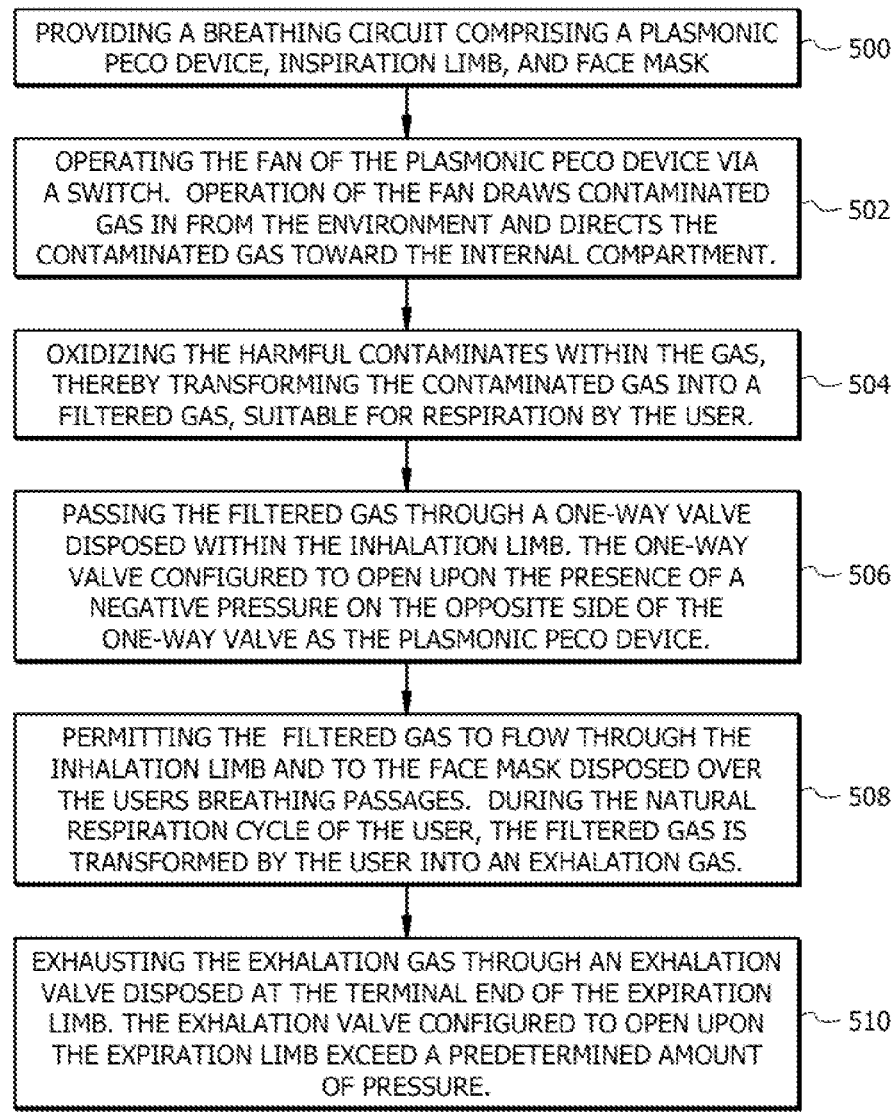
FIG. 10 is an exemplary process flow diagram depicting a method of removing harmful contaminants from a gas supplied to a user for respiration.

Referring now to FIG. 10, in conjunction with FIGS. 1-9, an exemplary process-flow diagram is provided, depicting a method of removing harmful contaminants from a gas supplied to a user for respiration. The steps delineated in the exemplary process-flow diagram of FIG. 10 are merely exemplary of a preferred order for removing harmful contaminants from a gas. The steps may be carried out in another order, with or without additional steps included therein. Additionally, the steps may be carried out with an alternative embodiment of the breathing system, as contemplated in the description above.

The method for removing harmful contaminants from a gas begins at step 500, during which the breathing system is provided. The breathing system includes the components discussed above. The method proceeds to step 502, during which the fan of the plasmonic PECO device is operated. Operation of the fan draws in contaminated gas from the environment and directs it to the internal compartment. As the harmful gas passes through the internal compartment, the contaminates undergo catalytic oxidation, thereby transforming the contaminated gas into a filtered gas in step 504. Specifically, photons emitted from the source of photons are incident on the nanotubes having a plasmonic layer and a photocatalyst. The photocatalyst, such as titanium dioxide, helps promote the catalytic oxidization of the contaminates, transforming the harmful, unclean gas into a clean, filtered gas.

In step 506, the filtered gas passes through a one-way valve upon a negative pressure being formed on the opposite side of the one-way valve as the plasmonic PECO device. In step 508, the filtered gas continues to flow through the inhalation limb and into the face mask disposed over the users breathing passages. During the user's natural respiration, the filtered gas is utilized and transformed into an exhalation gas. At step 510, the exhalation gas is forced into the exhalation limb of the face mask. As the user exhales, positive pressure builds in the inhalation limb, thereby closing the one-way valve. As the user continues to exhale, pressure continues to build until it overcomes the pressure required to open the exhaust valve disposed at the terminal end of the exhalation limb. At step 510, the exhalation gas is exhausted through the opened exhalation valve and dispersed into the surrounding environment.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A breathing purification system for delivering a gas from an environment to a user, the breathing purification system comprising:
    an inhalation limb including a first end in one way fluid communication with a face mask and a second opposite end in one way fluid communication with a plasmonic device; and
    the plasmonic device includes an internal compartment comprising:
        a source of photons having a wavelength and a filter, the filter including:
            a nanostructure having a length ⅓ to ¼ the wavelength;
            a plasmonic layer disposed on the nanostructure, the plasmonic layer including noble metal nanoparticles;
            a protective layer applied to the nanostructure, wherein the protective layer prevents oxidization of the noble metal nanoparticles of the plasmonic layer;
            the plasmonic layer disposed between the nanostructure and the protective layer;
        wherein the photons emitted by the source of photons are incident on the filter;
        whereby the gas from the environment is filtered within the internal compartment before being supplied to the user via the face mask.

2. The breathing purification system for delivering a gas from an environment to a user of claim 1, wherein the filter includes a photocatalyst.

3. The breathing purification system for delivering a gas from an environment to a user of claim 2, wherein the photocatalyst is titanium dioxide, zinc oxide, silicon dioxide, or titanium oxide doped with nitrogen or a metal.

4. The breathing purification system for delivering a gas from an environment to a user of claim 1, wherein the protective layer is less than 5 nm thick.

5. The breathing purification system for delivering a gas from an environment to a user of claim 4, wherein the protective layer is silicon oxide, a metal oxide, a salt, or a metal hydride.

6. The breathing purification system for delivering a gas from an environment to a user of claim 1, wherein the face mask comprises:
    an exhalation port disposed within a body of the face mask; and
    an exhalation limb including a first end in fluid communication with the exhalation portion and a second opposite end configured to exhaust an exhalation gas to the environment.

7. The breathing purification system for delivering a gas from an environment to a user of claim 6, wherein the exhalation limb includes an exhalation valve disposed between the first end and the second end of the exhalation limb, wherein the exhalation valve is configured to restrict a flow of the gas from the environment to an internal environment of the face mask.

8. The breathing purification system for delivering a gas from an environment to a user of claim 1, wherein the source of photons is a light source having a wavelength of about 320 nm to 395 nm.

9. The breathing purification system for delivering a gas from an environment to a user of claim 1, wherein the source of photons is visible light having a wavelength of about 400 nm to 700 nm.

10. The breathing purification system for delivering a gas from an environment to a user of claim 1, wherein the plasmonic layer is applied to the nanostructure by e-beam deposition or plasma deposition.

11. The breathing purification system for delivering a gas from an environment to a user of claim 1, wherein the plasmonic layer is applied to the nanostructure by a reduction reaction of a salt of the noble metal nanoparticles of the plasmonic layer.

12. The breathing purification system for delivering a gas from an environment to a user of claim 1, further comprising:
    a switch in electrical communication with a fan configured to draw the gas from the environment through the filter and into the inhalation limb,
    a pressure sensor configured to continuously monitor a pressure within the inhalation limb, such that when the pressure within the inhalation limb exceeds a predetermined pressure, the pressure sensor sends an electrical signal to the switch to turn off the fan, thereby preventing the over pressurization of the inspiration limb.

13. The breathing purification system for delivering a gas from an environment to a user of claim 1, wherein the nanostructure is a carbon nanostructure, a titanium oxide nanostructure, a metal nanostructure, a metal nanostructure, or a silicon oxide nanostructure.

14. The breathing purification system for delivering a gas from an environment to a user of claim 1, wherein the nanostructure is crushed, thereby increasing a surface area of the plasmonic layer when the plasmonic layer is deposited onto the crushed nanostructure.

15. The breathing purification system for delivering a gas from an environment to a user of claim 1, wherein the crushed nanostructure has a length between 50 nm to 100 nm.

16. The breathing purification system for delivering a gas from an environment to a user of claim 1, wherein the crushed nanostructure has a length between 20 nm to 100 nm.

17. A breathing purification system for delivering a gas from an environment to a user, the breathing purification system comprising:
- an inhalation limb including a first end in fluid communication with a face mask and a second opposite end in fluid communication with a plasmonic device;
- the plasmonic device including an internal compartment disposed within the plasmonic device, the internal compartment comprising:
  - a source of photons having a wavelength and a filter, the filter including:
    - a nanostructure having a length ⅓ to ¼ the wavelength;
    - a plasmonic layer disposed on the nanostructure via e-beam or plasma deposition, the plasmonic layer including noble metal nanoparticles;
    - a protective layer including a non-porous photocatalyst, the protective layer having a thickness of less than 20 nm, wherein the protective layer prevents oxidization of the noble metal nanoparticles of the plasmonic layer;
    - wherein the plasmonic layer is disposed between the nanostructure and the protective layer;
  - wherein the photons emitted by the source of photons are incident on the filter, thereby activating the photocatalyst; and
- a one-way valve disposed between the face mask and the plasmonic device, the one-way valve operable to transition between a closed configuration and an open configuration, wherein the closed configuration occurs as a result of positive pressure in the inhalation limb, and the open configuration occurs as a result of negative pressure in the inhalation limb;
- wherein the gas from the environment flows through the internal compartment of the plasmonic device, such that when the user inhales, the filtered gas is configured to flow to the face mask via the inhalation limb as a result of the negative pressure created when the user inhales.

18. The breathing purification system for delivering a gas from an environment to a user of claim 17, further comprising a regulation valve disposed between the face mask and the plasmonic device, the regulation valve configured to adjust a speed of a fan, thereby adjusting a flow rate of the gas through the internal compartment.

19. The breathing purification system for delivering a gas from an environment to a user of claim 17, wherein at least a portion of the face mask and the inhalation limb are coated with a compound that is toxic to microorganisms, wherein the compound is configured to reduce a chance of the user being infected.

20. A method of removing harmful contaminants from a gas supplied to a user for respiration, the method comprising the steps of:
- providing a breathing system configured to supply an amount of the gas to the user, the breathing system comprising:
  - an inhalation limb having a first end in fluid communication with a face mask and a second opposite end in fluid communication with a plasmonic device having an internal compartment disposed therein, the internal compartment comprising:
    - a source of photons having a wavelength and a filter, the filter including:
      - a nanostructure having a length ⅓ to ¼ the wavelength;
      - a plasmonic layer disposed on the nanostructure, the plasmonic layer including noble metal nanoparticles;
      - a protective layer including a photocatalyst, the protective layer disposed on the nanostructure having a thickness of less than 20 nm, wherein the protective layer prevents oxidization of the noble metal nanoparticles of the plasmonic layer;
      - the plasmonic layer being disposed between the nanostructure and the protective layer;
    - wherein the photons emitted by the source of photons are incident on the photocatalyst, thereby activating the photocatalyst;
- passing the gas from an environment through the internal compartment and into the inhalation limb, thereby removing harmful contaminants from the gas via catalytic oxidation of the harmful contaminants as the gas passes through the filter of the internal compartment; and
- operating a one-way valve disposed between the face mask and the plasmonic device, the one-way valve including a closed configuration and an open configuration, the closed configuration occurring when there is positive pressure within the inhalation limb, and the open configuration occurring when there is negative pressure in the inhalation limb,
- wherein when in the open configuration, the gas flows from the internal compartment where the gas is filtered to remove harmful contaminants, through the inhalation limb, and to the face mask of the user, thereby permitting the user to breathe the filtered gas during respiration.

* * * * *